(12) United States Patent
Johnson, Jr. et al.

(10) Patent No.: US 6,660,891 B2
(45) Date of Patent: Dec. 9, 2003

(54) METHODS FOR THE PRODUCTION OF D-CHIRO-INOSITOL AND THE USE OF D-CHIRO INOSITOL OBTAINED THEREFROM

(75) Inventors: Leland L. Johnson, Jr., Virginia Beach, VA (US); Mark C. Sleevi, Midlothian, VA (US); A. S. Campbell, Brighton, MA (US); Robert Plourde, Chapel Hill, NC (US); Patrick Leonard, Epping, NH (US); Paul Miller, Missoula, MT (US)

(73) Assignee: Insmed Incorporated, Glen Allen, VA (US)

( * ) Notice: Subject to any disclaimer, the term of this patent is extended or adjusted under 35 U.S.C. 154(b) by 203 days.

(21) Appl. No.: 09/853,032

(22) Filed: May 11, 2001

(65) Prior Publication Data

US 2002/0023877 A1 Feb. 28, 2002

Related U.S. Application Data

(60) Provisional application No. 60/204,391, filed on May 15, 2000.

(51) Int. Cl.$^7$ ............................................... C07C 35/16
(52) U.S. Cl. ......................................................... 568/833
(58) Field of Search ........................................... 568/833

(56) References Cited

U.S. PATENT DOCUMENTS

| | | | | |
|---|---|---|---|---|
| 2,112,553 A | * | 3/1938 | Bartow | |
| 2,691,011 A | * | 10/1954 | Perlman | |
| 5,091,596 A | | 2/1992 | Kennington et al. | 568/833 |
| 5,124,360 A | | 6/1992 | Larner et al. | 514/738 |
| 5,428,066 A | | 6/1995 | Larner et al. | 514/738 |
| 5,463,142 A | | 10/1995 | Riley et al. | 568/833 |
| 5,482,631 A | * | 1/1996 | Saska | |
| 5,550,166 A | | 8/1996 | Ostlund et al. | 514/715 |
| 5,714,643 A | | 2/1998 | Sato et al. | 538/833 |
| 5,827,896 A | | 10/1998 | Ostlund et al. | 514/715 |
| 5,932,774 A | | 8/1999 | Riley et al. | 568/833 |
| 6,162,795 A | | 12/2000 | Obendorf et al. | 514/35 |

OTHER PUBLICATIONS

Clark–Lewis, J. Chem. Soc., pp. 499–503 (1961).*
Vogel, "A Text–Book of Practical Organic Chemistry," 3$^{rd}$ Ed., pp. 122–130 (1957).*
International Search Report for International Application No. PCT/US01/15353, mailed Sep. 25, 2001.
Kessler, C. et al., "D–*chiro*–inositol Improves Insulin and Glucose Profiles in Human Subjects with Impaired Glucose Tolerance," *Diabetes* 47(Suppl. 1): A358, Abstract No. 1385, The American Diabetes Association (1998).
Nestler, J.E. et al., "Ovulatory and Metabolic Effects of D–*chiro*–inositol in the Polycystic Ovary Syndrome," *New Engl. Jour. Med. 340*:1314–1320, The Massachusetts Medical Society (1999).
Anderson, A.B., "Pinitol from Sugar Pine Stump Wood," *Indust. Eng. Chem. 45*:593–596, American Chemical Society (1953).

* cited by examiner

Primary Examiner—Michael L. Shippen

(57) ABSTRACT

The present invention relates to methods for the production and isolation of D-chiro-inositol (DCI) from plant extracts. Specifically the present invention provides a method to produce D-chiro-inositol from a precursor moiety by conversion in concentrated hydrochloric acid. More specifically, the present invention relates to a method for the efficient production of DCI by a process involving the extraction of D-pinitol from soy hulls followed by conversion thereof to DCI.

12 Claims, No Drawings

METHODS FOR THE PRODUCTION OF D-CHIRO-INOSITOL AND THE USE OF D-CHIRO INOSITOL OBTAINED THEREFROM

CROSS-REFERENCE TO RELATED APPLICATIONS

This application claims priority to U.S. Provisional Application No. 60/204,391, filed May 15, 2001, which is herein incorporated by reference.

BACKGROUND OF THE INVENTION

1. Field of the Invention

The present invention relates to methods for the production and isolation of D-chiro-inositol (DCI) from plant extracts. Specifically the present invention provides a method to produce D-chiro-inositol from a precursor moiety by hydrolysis in an aqueous acid, preferably HCl. More specifically, the present invention relates to a method for the efficient production of DCI by a process involving the extraction of D-pinitol from soy hulls followed by conversion thereof to DCI.

2. Background Art

D-chiro-inositol (DCI) is a rare isomer of inositol that has been implicated as having a role in the activity of insulin on anabolic metabolism. It has been found that insulin resistance correlates with deficiencies of DCI, and that supplementation with oral DCI improves insulin sensitivity in insulin resistant individuals. Clinical research supports the utility of DCI for treatment of diseases characterized by insulin resistance. For example, in a recent Phase II clinical study with 44 women afflicted with polycystic ovary syndrome (PCOS), administration of DCI (1200 mg/day for 6–8 weeks) resulted in ovulation by 86% of the patients, contrasted to ovulation in only 27% of the control (placebo) subjects (Nestler, J. E. et al., *New Engl. J. Med.* 340:1314–1320 (1999)). Similarly, in a clinical study of subjects with impaired glucose tolerance, administration of DCI (1200 mg/day for 2 weeks) restored glucose tolerance and insulin secretion to normal levels (Kessler et al., *Diabetes Abst. 58th Scientific Sessions*, #1385, A358 (1998)).

A source of DCI is the aminoglycoside kasugamycin, a fermentation product of *Streptomyces kasugaspinus* and *Streptomyces kasugaensis*, which contains a molecule of DCI bound through a glycosidic linkage to the aminosugar kasugamine. Treatment of kasugamycin with strong acid cleaves this glycosidic linkage, liberating DCI and kasugamine, along with various other nitrogen-containing side products.

Several processes exist for producing DCI from kasugamycin, each with unique attendant disadvantages or limitations. The first process disclosed (Kennington et al, U.S. Pat. No. 5,091,596) involved large quantities of ion-exchange resins being used to neutralize the hydrolysis mixture and to purify the DCI. A subsequent approach (Sato et al., U.S. Pat. No. 5,714,643) employed a strongly acidic ion exchange resin, rather than aqueous acid, to effect the hydrolysis, but also required large quantities of ion exchange resin to purify the resulting DCI.

As noted, both of these processes required large quantities of resin, and the subsequent costly evaporation of accompanying large quantities of aqueous solution. If these processes were scaled up to manufacture the quantities of DCI required to satisfy the PCOS or Type 2 diabetic population, the processing of such quantities of aqueous solution could be cost prohibitive.

Another approach for preparing DCI from kasugamycin is acetolysis (Riley et al., U.S. Pat. No. 5,463,142; U.S. Pat. No. 5,932,774). While this process obviated the need for ion exchange chromatography, it required a number of distinct process steps, including: (i) acetylation/hydrolysis of kasugamycin; (ii) purification of crude DCI hexaacetate; (iii) deacetylation of the purified hexaacetate; and (iv) isolation of DCI. Each step adds to the cost of the process and thus could limit the economic viability of manufacturing DCI using this approach.

Alternatively, D-Pinitol (the 3-O-methyl ether of DCI) may also serve as a useful precursor to DCI. Originally discovered in pine stumps (Anderson, *Indus. Eng. Chem.* 45:593:596 (1953)) D-pinitol is also present in a wide variety of renewable, leguminous plants including soy (see for example Oslund et al. U.S. Pat. Nos. 5,550,166 and 5,827,896). D-Pinitol has been found in virtually all parts of the soy plant including whole plant, whole beans, soy flour, flakes and hulls.

In view of its high therapeutic potential and the ongoing studies involving treatment with DCI, there remains a need in the art for a simple and efficient process to manufacture large quantities of DCI without any of the disadvantages of present methods.

BRIEF SUMMARY OF THE INVENTION

The present invention provides methods to produce D-chiro-inositol (DCI) from crude plant extracts containing at least one carbohydrate or oligosaccharide that comprises D-chiro-inositol as a structural component comprising the steps:

(a) preparing a reaction solution comprising a D-chiro-inositol precursor in a solution of about 6 N to 12 N HCl; and (b) reacting the solution of step (a) at a temperature in the range of about 65° C. to about 110° C. for a period of time sufficient to convert the D-chiro-inositol precursor to D-chiro-inositol.

Surprisingly, reaction of the plant extract carbohydrates in concentrated HCl results in the in conversion of most types of carbohydrates into an insoluble byproduct but does not affect the solubility or structural integrity of D-chiro-inositol. Therefore this single reaction provides D-chiro-inositol that is substantially free of other contaminating carbohydrates, thus eliminating the need for subsequent purification techniques.

The present invention also provides pharmaceutical formulations comprising DCI prepared by the methods provided herein and a pharmaceutically acceptable carrier. These formulations are useful in treating mammalian metabolic diseases where the causative factor or a complicating factor is characterized by abnormal glucose metabolism and/or decreased insulin sensitivity. These mammalian metabolic diseases include, but are not limited to, the following: diabetes mellitus and its chronic complications; gestational diabetes; pre-eclampsia; obesity; hyperlipidemia and/or dyslipidemia; atherosclerosis; hypertension; cardiovascular disease; AIDS; cancer; wasting and/or cachexia; sepsis; trauma, such as associated with burns, malnutrition and/or stress; aging; autoimmune diseases, such as lupus; endocrine diseases; hyperuricemia; polycystic ovary disease; and complications arising from athletic activity or inactivity.

DETAILED DESCRIPTION OF THE INVENTION

The phrase "D-chiro-inositol (DCI) precursor" as used herein refers to a plant extract containing one or more carbohydrates or oligosaccharides wherein at least a portion of which comprises a D-chiro-inositol moiety as a structural component. D-chiro-inositol (DCI) precursors may include, for example but not by way of limitation, D-chiro-inositol, D-pinitol (the 3-O-methyl ether of DCI), ciceritol (a pinitol digalactoside), 1D-2-O-alpha-D-galactopyranose-chiro-inositol, fagopyritols (alpha-galactosyl-D-chiro-inositol derivatives), and the like.

Preferred D-chiro-inositol precursors are plant extracts including pine needles, pine stumps, chick peas, orange peels, Bougainvillea leaves, alfalfa, soy beans, soy plant, soy flakes, soy hulls, and other legumes. In one embodiment, soy hulls are extracted to yield a D-chiro-inositol precursor containing a quantity of D-pinitol.

I. D-Chiro-Inositol Precursors Extraction from Plant Materials

According to this embodiment of the present invention, a quantity of plant material, such as soy hulls, is treated with a solvent or mixture of solvents under suitable time and temperature conditions so as to obtain a solution of the D-chiro-inositol precursors and other soluble products. The solvent or solvents may be any solvent known and available to those skilled in the art in which the D-chiro-inositol has a sufficient solubility to permit it to be separated from the plant material. Illustrative examples of suitable solvents include, but are not limited to, the following: water; acidified water; lower aliphatic alcohols, such as methanol, ethanol and isopropanol; and mixtures of water and one or more alcohols. The time and temperature employed for this step of the inventive process will depend upon the specifics of the extraction, such as the particular solvent employed, and may be determined empirically by one skilled in the art.

The solution of D-chiro-inositol may then be separated from the legume solids and other insoluble materials by any suitable means known to those skilled in the art, such as by filtration. Once separated, the solution of D-chiro-inositol is preferably concentrated by removal of sufficient solvent or solvents to provide an intermediate solid or semi-solid substance that contains crude D-chiro-inositol. Suitable means for concentrating the solution of D-chiro-inositol are known to those skilled in the art and include, but are not limited to, the following; distillation; spray drying; reverse osmosis; and combinations of two or more of these. A particular means for concentrating the solution of D-chiro-inositol will depend upon certain variables, including the particular solvent or solvents involved, and may be determined empirically by one skilled in the art.

The crude D-chiro-inositol contained in the intermediate solid or semi-solid substance may be directly converted to DCI, but may also be further purified.

The crude D-chiro-inositol may be further purified by any suitable means known to those skilled in the art. Suitable means for purifying the crude D-chiro-inositol are known to those skilled in the art and include, but are not limited to, additional solvent extraction and concentration.

In one embodiment of the present invention soy hulls are used as a starting material from which the D-chiro-inostitol precursor is derived. The use of soy hulls is used advantageously because they are a low-cost, renewable source of D-pinitol. In addition, the soy hull is composed largely of insoluble carbohydrate fiber and does not have significant amounts of lipid or protein, thus reducing the number of steps required to isolate the D-pinitol from other contaminants.

II. Preparation of DCI

One aspect of the invention involves the conversion of to D-chiro-inositol in a concentrated acid. Surprisingly the inventors discovered that D-chiro-inositol is stable under acidic conditions that destroy other sugars and demethylate D-Pinitol, thus yielding a higher purity product without needing subsequent chromatographic purification procedures. Thus a crude D-chiro-inositol composition comprising one or more components where at least 10% (w/w) of the mass is a D-chiro-inositol moiety is subject to concentrated acid in a solution of about 5 N to 12 N HCl at a temperature in the range of about 65° C. to about 110° C. for a period of time.

The D-chiro-inositol moiety component is present in at least 10% (w/w) of the crude extract, preferably greater than at least 25%, and most preferably greater than at least 50%.

The concentration of HCl in the final reaction volume is about 5 N to about 12 N, preferably about 9N to about 12N, and most preferably about 9N.

The temperature of the reaction is in the range of about 65° C. to about 110° C., preferably about 90° C. to about 110° C., and most preferably about 95° C. Advantageously the reaction can be conducted at atmospheric pressure, which is preferably for large-scale synthesis. The reaction pressure can be raised to reduce the reaction time as is well known in the art.

The D-chiro-inositol precursor is contacted with the HCl for a time sufficient to affect the complete cleavage of the precursor moeity to produce DCI. One skilled in the art may determine suitable reaction times empirically by monitoring the progress of the reaction. The progress of the reaction may be monitored by sampling the reaction mixture and analyzing the sample using any of the methods and techniques known and available to those skilled in the art, such as thin layer chromatography, gas chromatography, gas chromatography/mass spectroscopy, HPLC and nuclear magnetic spectroscopy. Generally the reaction times are about 3 hours to about 48 hours for reactions containing 5 N–12 N aqueous acid at 65° C. to 110° C. at atmospheric pressure.

In an exemplary embodiment of the present invention, a given quantity of D-pinitol is heated with a quantity of an aqueous acid sufficient to cleave the methyl group under the reaction conditions. For example, a quantity of 10% to 50% D-pinitol is adjusted to a reaction solution containing 5 N to 12N HCl and is reacted at about 95° C. for about 16 to about 18 hours.

Following hydrolysis and conversion of the D-chiro-inositol precursor to D-chiro-inositol, the byproducts may be removed by filtration through a decolorizing carbon such as Darco 60.

After filtration the DCI solution is adjusted to a concentration of at least about 25% (DCI mass to aqueous acid).

The DCI is precipitated from the DCI/acid solution by the addition of about 2 to about 8 volume-fold excess of a lower aliphatic alcohol (e.g. methanol, ethanol, or n-propanol), or a mixture of aliphatic alcohols over a period of about 0.5 hours to about 1.5 hours. Preferably the volume of aliphatic alcohol is added over a period of about 0.5 hours to about 1.5 hours at a temperature in the range of about 65° C. to about 75° C. Thereafter the precipitation reaction is cooled to ambient temperature (e.g. 15° C. to 30° C.) and the DCI solids are isolated by filtration.

After precipitation, the D-chiro-inositol may be used as a product or may be further purified by one or both of the following techniques:

(i) the DCI solids are dissolved in an appropriate amount of water, and the resulting aqueous solution is contacted with a sufficient quantity of ion exchange resin(s) to remove any remaining impurities; and/or (ii) the DCI solids are re-precipitated using a suitable solvent (or solvents) to remove any remaining impurities.

Preferably, the DCI solids are dissolved in a minimal quantity of water and the resulting DCI aqueous solution is contacted with a determined amount of one or more ion exchange resins. More preferably, the DCI solution is first contacted with a basic (anion) exchange resin, and then with an acidic (cation) exchange resin. This technique is particularly useful to remove any salt ions that remained in the solution after the original plant extraction techniques.

The amount of ion exchange resin is that amount of resin necessary to completely remove any remaining ionic impurities in the DCI aqueous solution, and will vary depending upon factors such as the type of resin employed and the length of time the DCI aqueous solution is contacted with the resin. Suitable amounts of the ion exchange resins may be determined empirically by one skilled in the art.

In another preferred embodiment of the present invention, the DCI is reprecipitated. Any suitable solvent or solvents may be used for reprecipitation the DCI, and one skilled in the art may determine such suitable solvents empirically.

Preferably, the DCI is reprecipitated by dissolving the DCI in a minimum amount of water and then adding an sufficient amount of anhydrous methanol or ethanol to the DCI aqueous solution to begin precipitation of the DCI. Optionally, the DCI aqueous solution may be heated and cooled, as is known to those skilled in the art, to facilitate crystallization.

In yet another preferred embodiment of the present invention, the DCI is first dissolved in a minimal quantity of water and the resulting DCI aqueous solution contacted with a determined amount of one or more ion exchange resins, then, following recovery, the DCI is reprecipitated using a suitable solvent or solvents.

III. Uses of DCI

The DCI produced in accordance with the present invention has a wide variety of potential uses. For example, DCI may be used for improving glucose metabolism and/or increasing insulin sensitivity in mammals, particularly humans. These mammals may have diabetes, particularly type 2 diabetes (insulin resistant diabetes), or may have only impaired glucose tolerance and have not yet developed diabetes.

In addition, DCI may be used for treating mammalian metabolic diseases characterized by abnormal glucose metabolism and/or decreased insulin sensitivity. These mammalian metabolic diseases include, but are not limited to, the following: diabetes mellitus and its chronic complications; gestational diabetes; pre-eclampsia; obesity; hyperlipidemia and/or dyslipidemia; atherosclerosis; hypertension; cardiovascular disease; AIDS; cancer; wasting and/or cachexia; sepsis; trauma, such as associated with burns, malnutrition and/or stress; aging; autoimmune diseases, such as lupus; endocrine diseases; hyperuricemia; polycystic ovary disease; and complications arising from athletic activity or inactivity.

DCI obtained in accordance with the present invention can also comprise the active component in a pharmaceutical composition. The pharmaceutical compositions of DCI may be administered to any animal that would benefit therefrom, particularly humans.

These pharmaceutical compositions will be formulated and dosed in a fashion consistent with good medical practice, taking into account the clinical condition of the individual patient (especially the side effects of treatment with the active agent), the site of delivery of the composition, the method of administration, the scheduling of administration, and other factors known to practitioners. The "effective amount" of each active agent (i.e. DCI or a derivative thereof) for the purposes of the present invention is determined in view of such considerations. Those skilled in the art can readily determine empirically an appropriate "effective amount" of each active agent for a particular mammalian patient.

DCI produced according to the present invention may also be administered pharmacologically as a prodrug. The expression "prodrug" as used herein denotes a derivative of DCI which is converted to DCI in vivo by an enzymatic or chemical process but exhibits enhanced delivery characteristics and/or therapeutic value. The preparation and administration of prodrugs of saccharides, for example in the form of methylated or acetylated hydroxyl groups, is well known in the art. (Baker, D. C., et al., *J. Med. Chem.* 27:270–274 (1984)).

As used herein, the phrase "pharmaceutically acceptable" is intended to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable carrier" is a pharmaceutically acceptable material, composition or vehicle, such as a liquid or solid filler, diluent, excipient, solvent or encapsulating material, involved in carrying or transporting the active agents of the inventive compositions from one organ, or portion of the body, to another organ, or portion of the body. Each carrier must be "acceptable" in the sense of being compatible with the other ingredients of the formulation and not injurious to the patient.

Some illustrative examples of materials which can serve as pharmaceutically-acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the inventive pharmaceutical compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredients which can be combined with a carrier material to produce a single dosage form will generally be that amount of each active ingredient which, together, produce the desired therapeutic effect. Generally, out of one hundred per cent, this amount will range from about 0.01 per cent to about ninety-nine percent of active ingredients, preferably from about 0.1 per cent to about 90 per cent, most preferably from about 1 per cent to about 90 per cent.

In general, the formulations are prepared by uniformly and intimately bringing into association the active ingredient with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of each active ingredient. The active ingredients of the inventive compositions may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredients can also be in micro-encapsulated form, if appropriate, with one or more of the above-described excipients.

Liquid dosage forms for oral administration of the inventive compositions include pharmaceutically acceptable emulsions, microemulsions, solutions, suspensions, syrups and elixirs. In addition to the active ingredients, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredients, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredients of the present invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredients. Formulations of the present invention which are suitable for vaginal administration also include pessaries, tampons, creams, gels, pastes, foams or spray formulations containing such carriers as are known in the art to be appropriate.

Dosage forms for the topical or transdermal administration of the inventive compositions include powders, sprays, ointments, pastes, creams, lotions, gels, solutions, patches and inhalants. The active ingredient may be mixed under sterile conditions with a pharmaceutically-acceptable carrier, and with any preservatives, buffers, or propellants which may be required.

Ophthalmic formulations, eye ointments, powders, solutions, drops, sprays and the like, are also contemplated as being within the scope of this invention.

Pharmaceutical compositions of this invention suitable for parenteral administration comprise DCI (or a derivative thereof) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Illustrative examples of suitable aqueous and nonaqueous carriers which may be employed in the pharmaceutical compositions of the invention include, but are not limited to, the following: water; ethanol; polyols, such as glycerol, propylene glycol, polyethylene glycol, and the like, and suitable mixtures thereof; vegetable oils, such as olive oil; and injectable organic esters, such as ethyl oleate. Proper fluidity can be maintained, for example, by the use of coating materials, such as lecithin, by the maintenance of the required particle size in the case of dispersions, and by the use of surfactant.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

When the compounds of the present invention are administered as pharmaceuticals, to humans and animals, they can be given alone or as a pharmaceutical composition containing, for example, 0.01 to 99.5% (more preferably, 0.1 to 90%) of each active ingredient together in combination with at least one pharmaceutically acceptable carrier.

The preparations of the present invention may be given orally, parenterally, topically, or rectally. They are of course given by forms suitable for each administration route. Oral administration is particularly preferred.

The phrases "parenteral administration" and "administered parenterally" as used herein are intended to mean modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein are intended to mean the administration of a compound, drug or other material other than directly into the central nervous system, such that it enters the patient's system and, thus, is subject to metabolism and other like processes, for example, subcutaneous administration.

The inventive compositions may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the active ingredients of the present invention, which may be used in a suitable hydrated form, and/or the pharmaceutical compositions of the present invention, are formulated into pharmaceutically acceptable dosage forms by conventional methods known to those of skill in the art.

As noted, actual dosage levels of the active ingredient in the inventive pharmaceutical compositions may be varied so as to obtain an amount which is effective to achieve the desired therapeutic response for a particular patient, composition, and mode of administration, without being toxic to the patient.

The selected dosage level will depend upon a variety of factors, including, but not limited to, the following: the activity of DCI (or the derivative thereof); the route of administration; the time of administration; the rates of absorption, distribution, metabolism and/or excretion of the particular active ingredient being employed; the duration of the treatment; other drugs, compounds and/or materials used in combination with the particular active ingredients employed; the age, sex, weight, condition, general health and prior medical history of the patient being treated; and like factors well known in the medical arts.

A physician or veterinarian having ordinary skill in the art can readily determine the effective amount of the active ingredient required in the inventive pharmaceutical compositions. For example, the physician or veterinarian could start doses of the pharmaceutical composition at levels lower than that required in order to achieve the desired therapeutic effect and gradually increase the dosage until the desired effect is achieved.

If desired, the effective daily dose of the active ingredients may be administered as two, three, four, five, six or more sub-doses administered separately at appropriate intervals throughout the day, optionally, in unit dosage forms.

Therapeutic compositions can be administered with medical devices known in the art. For example, a therapeutic composition of the present invention can be administered with a needleless hypodermic injection device, such as the devices disclosed in U.S. Pat. Nos. 5,399,163; 5,383,851; 5,312,335; 5,064,413; 4,941,880; 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4.,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are well known to those skilled in the art.

Having now fully described this invention, it will be understood to those of ordinary skill in the art that the methods of the present invention can be carried out with a wide and equivalent range of conditions, formulations, and other parameters without departing from the scope of the invention or any embodiments thereof. All patents and publications cited herein are hereby fully incorporated by reference in their entirety.

The following examples illustrate the present invention without, however, limiting the same thereto.

EXAMPLES

Example 1

Preparation of D-chiro-Inositol from Soya Hulls a) Initial Aqueous Extraction

Water, acidified to pH 4.5 with dilute HCl, was added to course ground soya hull in a ratio of 8 parts water to 1 of hulls (w/w), and stirred at 40° C. for 50 min. The mixture was then filtered first through cheesecloth and then though a course Buchner funnel. The insoluble filter cake was washed with water approximately one-tenth of that used in the initial extraction. The combined soluble extraction solution and washings were concentrated under reduced pressure to afford a fine flaky tan solid. In six experiments in which 20 to 1250 g of soya hulls were extracted, an average of 9.57% of the initial weight of the hulls was recovered on concentration of the aqueous solution. Samples of these materials were analyzed by HPLC as described below and found to contain an average of 11.7% pinitol by weight.

b) Aqueous Methanol Extraction

The pinitol-containing solid from the aqueous extraction was stirred at reflux in 10% aqueous methanol (5 mL per g solid) for 30 minutes. Following hot filtration, the filter cake was washed with hot 10% aqueous methanol (1.66 mL per g solid) and the combined filtrate and washings were concentrated. The residue was found to contain 18.5% to 38% of the mass of the aqueous extract and to be 20 to 29% by weight pinitol by HPLC analysis.

c) Treatment With Acid and Isolation of DCI

The pinitol containing material from the aqueous methanol extraction was stirred in 9N HCl (10 mL per g extract) and heated to 105° C. for 12 hours. The mixture was cooled, treated with activated charcoal (0.65 g per g extract), filtered and the filter cake washed with water. The combined filtrate and washings were concentrated under reduced pressure. The residue was stirred with methanol (1 mL per g extract) and n-propyl alcohol (1.5 mL per g extract) was added in small portions. After the addition was completed, the mixture was stirred for 30 minutes. The precipitate was collected by filtration and dissolved in deionized water (5 mL per g extract). The solution was treated with AG501-X8 mixed bed ion exchange resin (0.225 g per g of extract), stirred for 2 hours and filtered. Concentration of the filtrate and drying under vacuum afforded 0.205 g of DCI per g of methanolic extract, which was identical (NMR, HPLC) to an authentic DCI standard.

d) HPLC Method for Determination of Pinitol and D-chiro-inositol

For pinitol determination, standards were made in the values of 0.625 mg/ml, 2.5 mg/ml, and 10 mg/ml by serial dilution from a 10 mg/ml pinitol standard. The D-chiro-inositol standard curve was determined using 1.25 mg/ml, 5 mg/ml, and 10 mg/ml from an in-house standard DCI (Lot 6119YS). Twenty microliters of each standard solution (in triplicate) was injected on a Waters 515 pump at 2 ml/min (81:19 acetonitrile/$H_2O$) and passed through an Econosphere $NH_2$5 u column. The detector was a Waters 310 Differential Refractometer, and all data was plotted on a Waters 746 Data Module. A plot of the average area vs. the concentration was arranged and analyzed by linear regression for goodness of fit. The unknown sample was injected (20 ul×3) and related to the standard curve. All concentrations of the unknown samples were held constant at 10 mg/ml.

Example 2

Production of D-Chiro-inositol From Enriched D-Pinitol

D-Pinitol (50 g,~90%; commercially available pine extract, New Zealand Pharmaceuticals) in a 500 ml round bottom flask was suspended in 200 ml of 9N HCl with magnetic stirring. The flask was placed in an oil-bath, set to 95–100° C., and a reflux apparatus was attached. The temperature was maintained for 18 hours, at which time, the heat was removed and the solution was allowed to cool to 23° C. Water (100 ml distilled, de-ionized) was added to bring the solution to ~5N. Activated charcoal (500 mgs, Darco G60) was added and stirred for 30 minutes. The suspension was filtered through a bed of Celite (5 g in medium fritted funnel) into a tared 1000 ml flask. The filter was rinsed with DDI water (2×100 ml), and the resulting solution was concentrate using rotary evaporation (20 mm, 60° C.) to a weight of 86 g, approximately 1:1 w:w expected DCI to aqueous HCl.

To the 1000 ml flask was added a magnetic stir-bar. The flask was placed in an oil bath set to 70° C., under reflux conditions, affixed with an equalization funnel charged with SD 3A ethyl alcohol (323 ml, 7.5 equivalents). The alcohol was added over the course of 1 hour, and the heating was maintained (60–70° C.) during the addition and for 1 hour following. At that time, the suspension was allowed to cool to 23° C. The suspension was filtered, and the crystals were dried.

An aqueous solution of the DCI containing material was de-ionized by treatment with Amberlite MB-3A ion exchange resin to give 42.00 g (>95%) of DCI. The DCI (42.00 g) was dissolved in DDI water (42 ml) in a 500 ml RBF. The flask was placed in an oil bath set to 70 C., under reflux conditions, affixed with an equalization funnel charged with SD 3A ethyl alcohol (315 ml, 7.5 equivalents). The alcohol was added over the course of 1 hour, and the temperature was maintained (60–70° C.) during the addition and for 1 hour following. At that time, the suspension was allowed to cool to 23° C. The suspension was filtered, and the crystals were dried overnight in a vacuum oven (10 mm, 60° C.) to produce 39.10 g of DCI, mp 250–252° C.

What is claimed is:

1. A method to produce D-chiro-inositol comprising:
   (a) preparing a reaction solution comprising a crude plant extract comprising a D-chiro-inositol precursor containing a D-chiro-inositol moiety selected from the group consisting of D-chiro-inositol, D-pinitol, ciceritol, 1D-2-O-alpha-D-galactopyranose-chiro-inositol, and fagopyritols in a solution of about 9 N to 12 N HCl; and
   (b) reacting the solution of step (a) at a temperature in the range of about 65° C. to about 110° C. for a period of time sufficient to convert the D-chiro-inositol precursor to D-chiro-inositol.

2. The method of claim 1 wherein the reaction solution comprises a D-chiro-inositol precursor in a solution of about 9 N HCl.

3. The method of claim 1 wherein the reaction temperature is in the range of about 90° C. to about 110° C.

4. The method of claim 1 further comprising the steps:
   (c) filtering the reaction solution of step (b) through decolorizing carbon;
   (d) adjusting the solution of step (c) to a concentration of at least about 25% D-chiro-inositol; and
   (e) precipitating the D-chiro-inositol from the reaction solution of step (d) with an aliphatic alcohol or mixture of at least two aliphatic alcohols.

5. The method of claim 4 wherein the D-chiro-inositol is precipitated by dilution of the solution of step (d) with about 2-fold to about 8-fold volume excess of the aliphatic alcohol or aliphatic alcohol mixture.

6. The method of claim 4 wherein the D-chiro-inositol is precipitated by dilution of the solution of step (d) with about 2-fold to about 8-fold volume excess of the aliphatic alcohol or aliphatic alcohol mixture while maintaining the resultant solution at a temperature of about 65° C. to about 75° C. during the course of alcohol dilution.

7. The method of claim 4 further comprising the steps;
   (f) dissolving the precipitated D-chiro-inositol of step (e) in an aqueous solution; and
   (g) removing contaminating ions with at least one ion exchange resin.

8. The method of claim 4 further comprising the steps;
   (f) dissolving the precipitated D-chiro-inositol of step (e) in an aqueous solution and reprecipitating the D-chiroinositol with and aliphatic alcohol or mixture of at least two aliphatic alcohols.

9. The method of claim 4 further comprising the steps;

(f) dissolving the precipitated D-chiro-inositol of step (e) in an aqueous solution;

(g) removing contaminating ions with at least one ion exchange resin; and (h) reprecipitating the D-chiro-inositol with an aliphatic alcohol or mixture of at least two aliphatic alcohols.

10. A method to produce D-chiro-inositol comprising:

(a) preparing a reaction solution comprising a crude plant extract containing one or more carbohydrates or oligosaccharides, wherein the extract comprises a D-chiro-inositol moiety selected from the group consisting of D-chiro-inositol, D-pinitol, ciceritol, 1D-2-O-alpha-D-galactopyranose-chiro-inositol, and fagopyritols, in a solution of about 9 N to 12 N HCl; and (b) reacting the solution of step (a) at a temperature in the range of about 90° C. to about 110° C. for a period of time sufficient to convert the D-chiro-inositol moiety to D-chiro-inositol.

11. The method of claim 10 further comprising:

(c) filtering the reaction solution of step (b) through decolorizing carbon;

(d) adjusting the solution of step (c) to a concentration of at least about 25% D-chiro-inositol; and (e) precipitating the D-chiro-inositol from the reaction solution of step (d) by diluting the solution of step (d) with about 2-fold to about 8-fold volume excess of the aliphatic alcohol or a mixture of at least two aliphatic alcohols while maintaining the resultant solution at a temperature of about 65° C. to about 75° C. during the course of alcohol dilution.

12. The method of claim 10 wherein the plant extract is obtained from soy hulls.

* * * * *